(12) United States Patent
Yamada et al.

(10) Patent No.: US 10,302,549 B2
(45) Date of Patent: May 28, 2019

(54) HANDRAIL FRICTION CHECKING DEVICE

(71) Applicant: Otis Elevator Company, Farmington, CT (US)

(72) Inventors: Takahiro Yamada, Narita (JP); Atsushi Yamada, Narita (JP); Hiromitsu Miyajima, Inzai (JP); Kenji Komiya, Chiba (JP)

(73) Assignee: OTIS ELEVATOR COMPANY, Farmington, CT (US)

( * ) Notice: Subject to any disclaimer, the term of this patent is extended or adjusted under 35 U.S.C. 154(b) by 237 days.

(21) Appl. No.: 15/371,487

(22) Filed: Dec. 7, 2016

(65) Prior Publication Data

US 2018/0156714 A1 Jun. 7, 2018

(51) Int. Cl.
*G01N 19/02* (2006.01)
*B66B 25/00* (2006.01)
*B66B 31/02* (2006.01)

(52) U.S. Cl.
CPC .......... *G01N 19/02* (2013.01); *B66B 25/006* (2013.01); *B66B 31/02* (2013.01)

(58) Field of Classification Search
CPC .......... G01N 19/02; B66B 25/06; B66B 31/02
USPC .............................................................. 73/9
See application file for complete search history.

(56) References Cited

U.S. PATENT DOCUMENTS

| 4,134,883 A | 1/1979 | Mendelsohn et al. |
| 5,092,446 A | 3/1992 | Sullivan, Jr. et al. |
| 5,563,392 A * | 10/1996 | Brown ................ B65G 43/02 235/91 R |
| 6,247,575 B1 * | 6/2001 | Thiel .................... B66B 1/44 198/330 |
| 8,061,215 B2 * | 11/2011 | Caunce ................ G01L 5/102 73/826 |
| 2006/0237284 A1 | 10/2006 | Miessbacher |

FOREIGN PATENT DOCUMENTS

| DE | 10141412 A1 | 3/2003 |
| JP | S5855831 A | 4/1983 |
| JP | H03192091 A | 8/1991 |
| JP | H0570077 A | 3/1993 |
| JP | H05105383 A | 4/1993 |
| JP | H09272687 A | 10/1997 |
| JP | 2001302164 A | 10/2001 |
| JP | 2004224553 A | 8/2004 |

(Continued)

OTHER PUBLICATIONS

European Search Report for application EP 17204921.5, dated Apr. 20, 2018, 16 pages.

*Primary Examiner* — John Fitzgerald
*Assistant Examiner* — Jean F Morello
(74) *Attorney, Agent, or Firm* — Cantor Colburn LLP

(57) ABSTRACT

A handrail friction checking device comprises a handrail gripper for gripping the handrail and movable together with the handrail, a spring with one end of the spring being fixed and the other end being connected to the handrail gripper so that the spring can apply a spring force which is opposed to the direction of handrail movement to the handrail gripper when the handrail gripper moves along with the handrail and a sensor which is disposed in a way that it is distanced from the handrail gripper and can be triggered by the handrail gripper when the handrail gripper moves along with the handrail.

12 Claims, 11 Drawing Sheets

(56) References Cited

FOREIGN PATENT DOCUMENTS

| | | | |
|---|---|---|---|
| JP | 2006151662 | A | 6/2006 |
| JP | 2006182534 | A | 7/2006 |
| JP | 2006306607 | A | 11/2006 |
| JP | 2008037601 | A | 2/2008 |
| JP | 2008265941 | A | 11/2008 |
| JP | 2008265971 | A | 11/2008 |
| JP | 2010006485 | A | 1/2010 |
| JP | 2013184792 | A | 9/2013 |

* cited by examiner

HANDRAIL FRICTION CHECKING DEVICE

BACKGROUND

This invention generally relates to passenger conveyors. More particularly, this invention relates to a device for checking the frictional driving force for a handrail of a passenger conveyor.

Passenger conveyors have proven effective for carrying people between different levels within a building or across an elongated pathway, for example. Typical arrangements include a plurality of steps or a belt upon which an individual stands to be carried from one location to another. A handrail typically rides over a balustrade and provides a surface for an individual to grab onto for stabilizing themselves.

Handrails are driven to move in unison with the steps or moving belt. A handrail drive mechanism causes the desired movement of the handrail. Typical arrangements rely upon wheels or rollers that frictionally engage the handrail to generate enough friction to drive the handrail in the desired direction.

A fabric layer is provided on the side of the handrail opposite the side grabbed by an individual to allow the handrail to readily slide along a guide to follow the balustrade. The same surface is frictionally engaged by the handrail drive mechanism. The friction caused by the wheels or rollers in the handrail drive mechanism tends to wear the fabric layer. As this fabric layer becomes worn, the handrail eventually can not operate as desired and requires repair or replacement.

Further, misalignment or displacement of the wheels or rollers in the handrail drive mechanism may also affect the frictional driving force of the handrail. Therefore, it is necessary to check on a regular basis if there is a sufficient frictional force for driving the handrail.

BRIEF SUMMARY

According to one embodiment of the invention, a handrail friction checking device comprises a handrail gripper for gripping the handrail and movable together with the handrail, a spring with one end of the spring being fixed and the other end being connected to the handrail gripper so that the spring can apply a spring force which is opposed to the direction of handrail movement to the handrail gripper when the handrail gripper moves along with the handrail and a sensor which is disposed in a way that it is distanced from the handrail gripper and can be triggered by the handrail gripper when the handrail gripper moves along with the handrail. The handrail friction checking device may further comprise a base fixed to a structural component and connected to one end of the spring, an intermediate member connected to the other end of the spring and a connecting member connecting the intermediate member to the handrail gripper.

The detailed description explains embodiments of the invention, together with advantages and features, by way of example with reference to the drawings.

DETAILED DESCRIPTION

Figure 1:
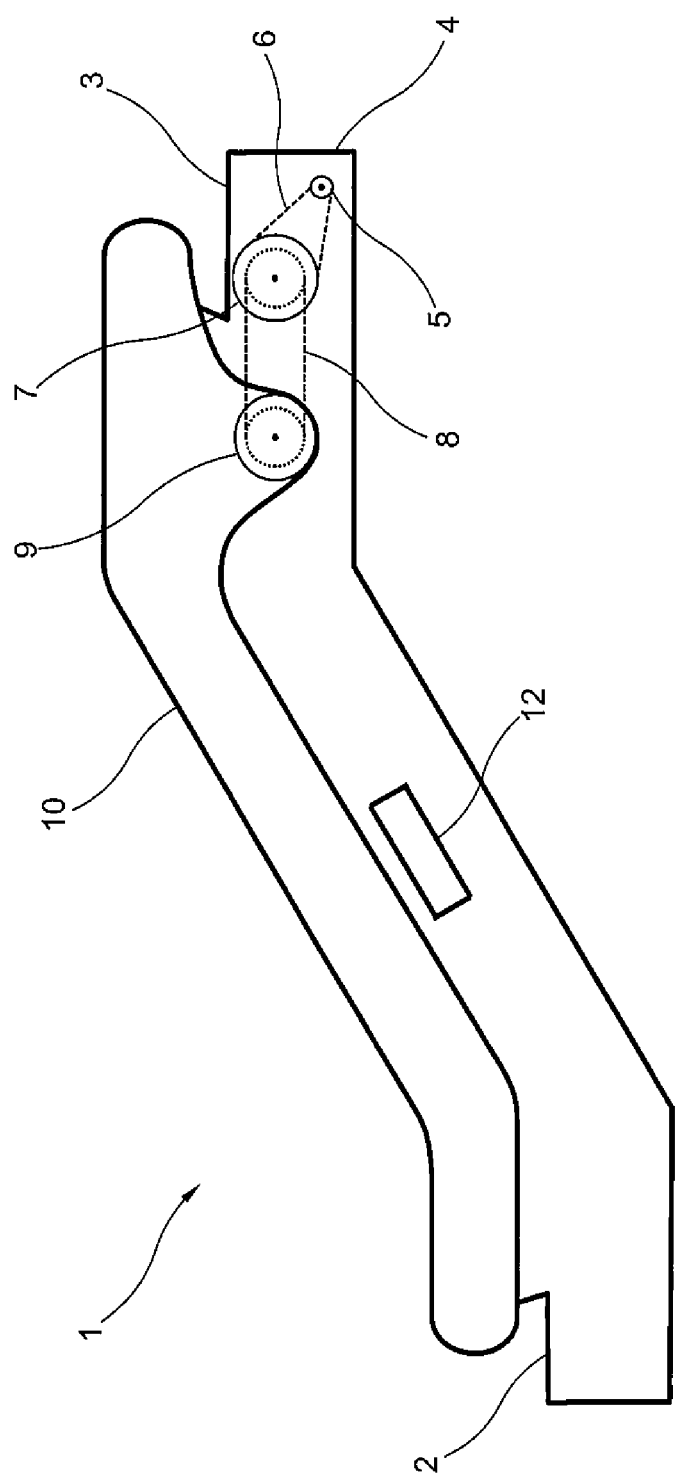
FIG. 1 is a schematic representation of an example passenger conveyor.

FIG. 1 schematically shows a passenger conveyer 1. In this example, the passenger conveyor 1 is an escalator having a plurality of steps for carrying passengers between landings at different levels within a building. This invention is not limited to escalators but is also applicable to other forms of passenger conveyors 1 such as moving walkways, for example.

The example passenger conveyor 1 of FIG. 1 comprises a truss 4 installed between a lower landing 2 and an upper landing 3. An escalator drive device 5 is located in the upper end of the truss 4 and is connected via a chain 6 to a sprocket wheel 7 of a step chain drive mechanism which drives a plurality of steps along a closed loop. The sprocket wheel 7 is in turn connected via a chain 8 to a friction wheel 9 of a handrail drive mechanism to transfer a driving force thereto. The friction wheel 9 drives a handrail 10 along a closed loop by frictional engagement with the inside surface thereof, i.e., the surface opposite the surface grasped by a passenger.

Figure 4:
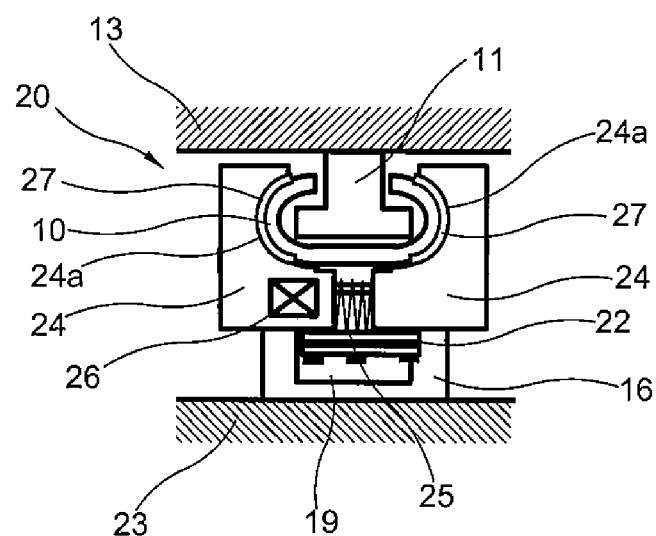
FIG. 4 is a cross sectional view of a handrail gripper of the load applying device shown in FIG. 3.

A handrail friction checking device 12 of the present invention is positioned in the return path of the handrail 10. One handrail friction checking device 12 may be provided for each handrail 10. The handrail 10 may be of the conventional flexible construction having a C-shaped cross section as shown in FIG. 4. A conventional T-shaped handrail guide 11 is located within the cross section of the handrail 10 to serve as a guide means. In the return path of the handrail 10, the handrail guide 11 is supported on a structural component 13 of the truss 4.

Figure 2:
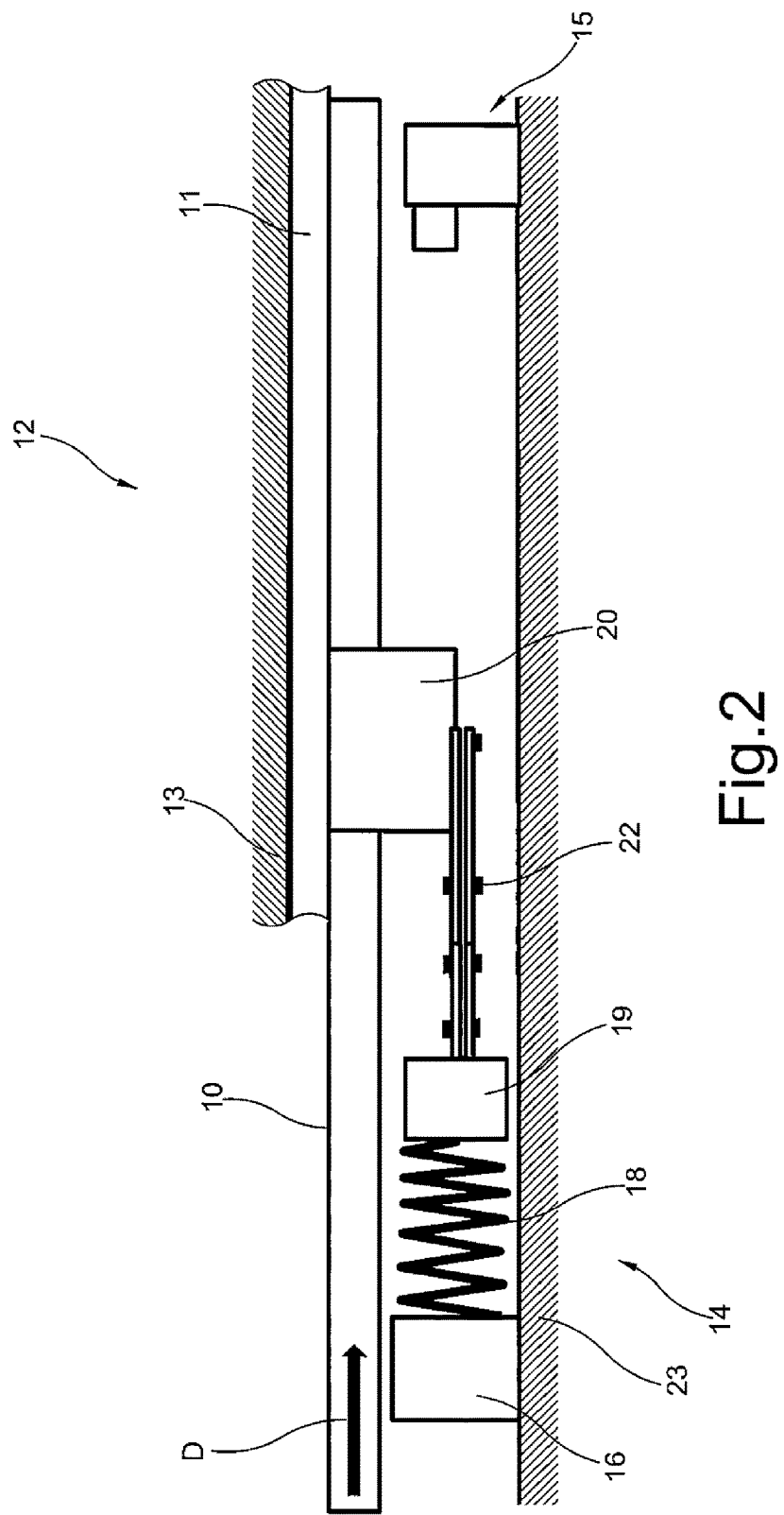
FIG. 2 is a side view of a handrail friction checking device of the present invention.
Figure 3:
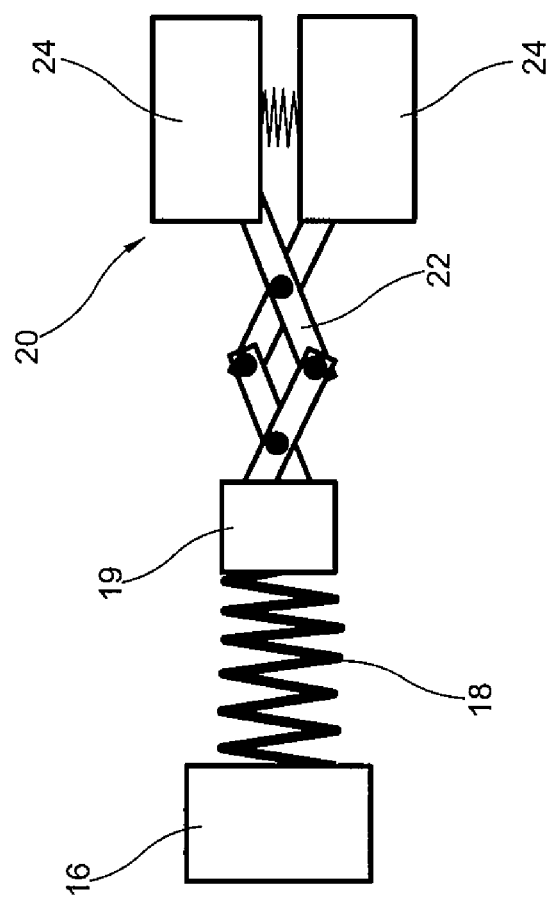
FIG. 3 is a plan view of a load applying device of the handrail friction checking device shown in FIG. 2.

With reference to FIGS. 2 to 4, the handrail friction checking device 12 is positioned just below the handrail 10 and comprises a load applying device 14 and a sensor 15. In a test mode, the handrail 10 is driven in direction D along the handrail guide 11. The load applying device 14 comprises a base 16, a coil spring 18 connected between the base 16 and an intermediate member 19, a handrail gripper 20 for gripping the handrail 10 and a connecting member 22 which connects the handrail gripper 20 to the intermediate member 19. The sensor 15 comprises a limit switch in this embodiment but may be any kind of sensor which is able to detect movement of the handrail gripper 20 such as a proximity sensor. The base 16 and the sensor 15 are fixed on a structural component 23 of the truss 4. The intermediate member 19 and handrail gripper 20 are guided to slide in the longitudinal direction in parallel with the handrail 10 such as by a sliding mechanism (not shown) which may include a guide rail and a sliding element. In this embodiment, the connecting member 22 is a pantograph.

Figure 5:
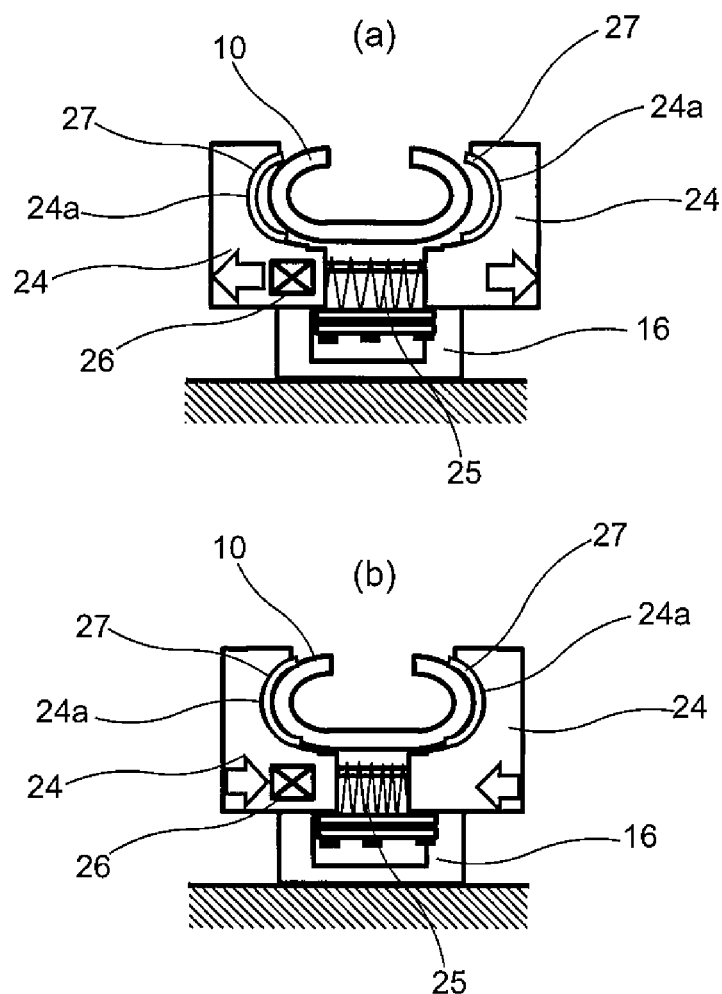
FIG. 5 shows the handrail gripper of FIG. 4 in a de-energized and energized state.

As shown in FIGS. 3 to 5, the handrail gripper 20 comprises a pair of gripping elements 24 each having an inner surface 24a shaped complementary to one side of the outer surface of the handrail 10, i.e., the surface grasped by a passenger. The gripping elements 24 are slidable in the lateral direction with respect to one another by a conventional means and biased by a spring 25 in a direction away from each other. At least one of the gripping elements 24 comprises an electromagnet 26 and the other of the gripping elements comprises an iron portion.

When the electromagnet 26 is not energized, the gripping elements 24 are biased in a direction away from each other and away from the handrail 10 by the spring 25, as shown in FIG. 5(a). When the electromagnet 26 is energized, the gripping elements 24 are attracted toward each other to firmly grip the outer surface of the handrail 10, as shown in FIG. 5(b). A slip stopper 27 such as a rubber element may be provided on the inner surface 24a of each of the gripping elements 24 to allow a firm grip of the gripping elements 24 on the handrail 10.

Figure 6:
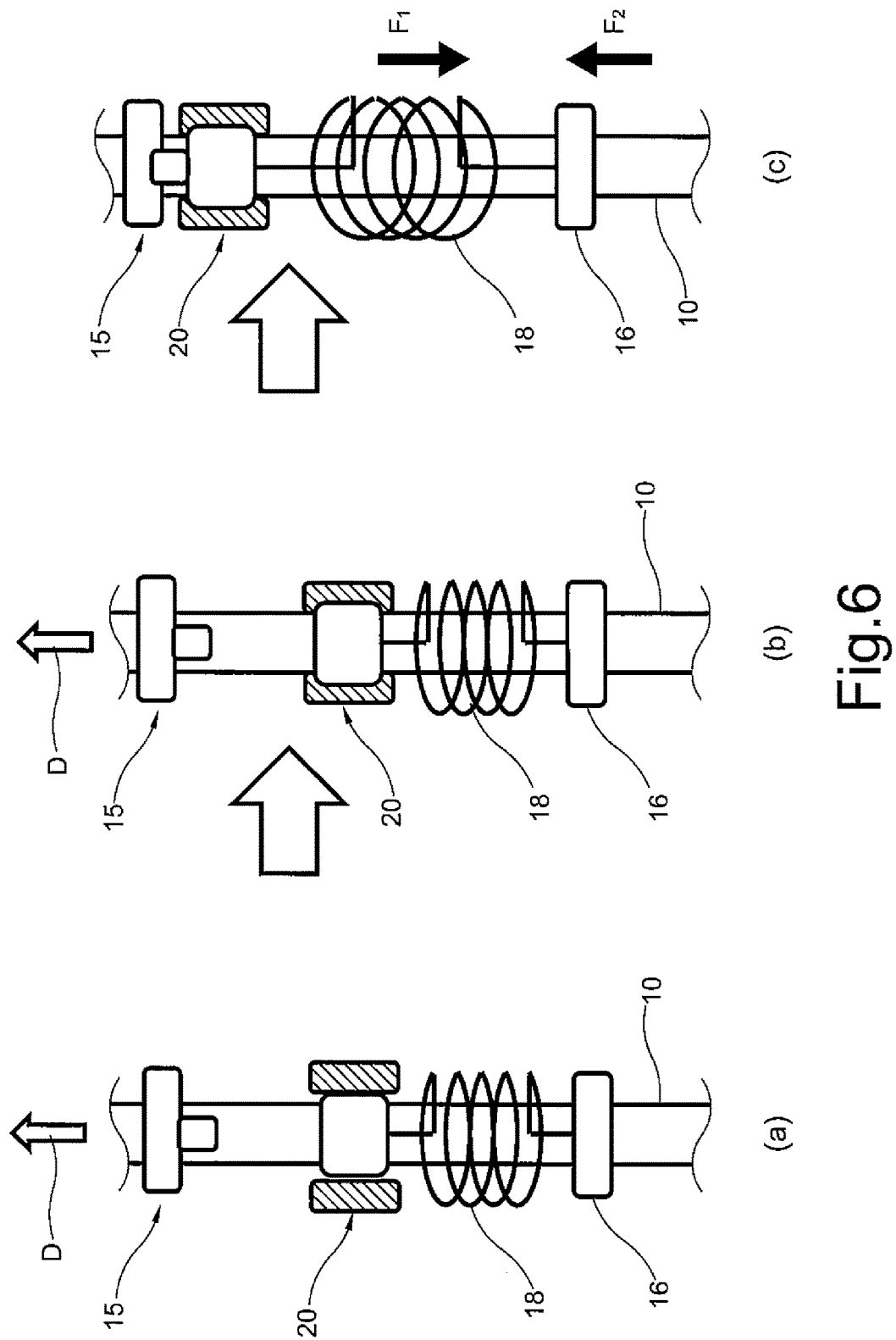
FIG. 6 is a schematic view showing the operation of the handrail friction checking device.

FIG. 6 shows how the handrail friction checking device 12 operates. When the handrail friction checking device 12 is not operating, i.e., the handrail gripper 20 is not energized, the handrail 10 is allowed to freely move through the gripping elements 24, as shown in FIG. 6(a). The limit switch 15 is in an OFF state.

When a test using the handrail friction checking device 12 is started, the handrail gripper 20 is energized to firmly grip the handrail 10 such that the handrail gripper 20 travels with the handrail 10, as shown in FIG. 6(b). As the handrail gripper 20 moves toward the limit switch 15, the coil spring 18 extends to apply a spring force on the handrail 10. In FIG. 6(c), the handrail gripper 20 has reached the limit switch 15 and has turned the limit switch 15 ON. In this position, a spring force $F_1$ is applied on the handrail 10 which is proportional to the distance the coil spring 18 has extended.

The fact that the limit switch 15 is switched ON indicates that the frictional driving force $F_2$ of the handrail is sufficiently large. Specifically, it indicates that the frictional driving force $F_2$ of the handrail is larger than the spring force $F_1$ plus the traveling resistance between the handrail 10 and the handrail guide 11. When the limit switch 15 is not switched ON, it indicates that the frictional driving force $F_2$ of the handrail is not sufficient. Specifically, it indicates that the frictional driving force $F_2$ of the handrail is insufficient such that slippage between the friction wheel 9 and handrail 10 occurs, preventing the handrail gripper 20 to reach the limit switch 15.

Figure 7:
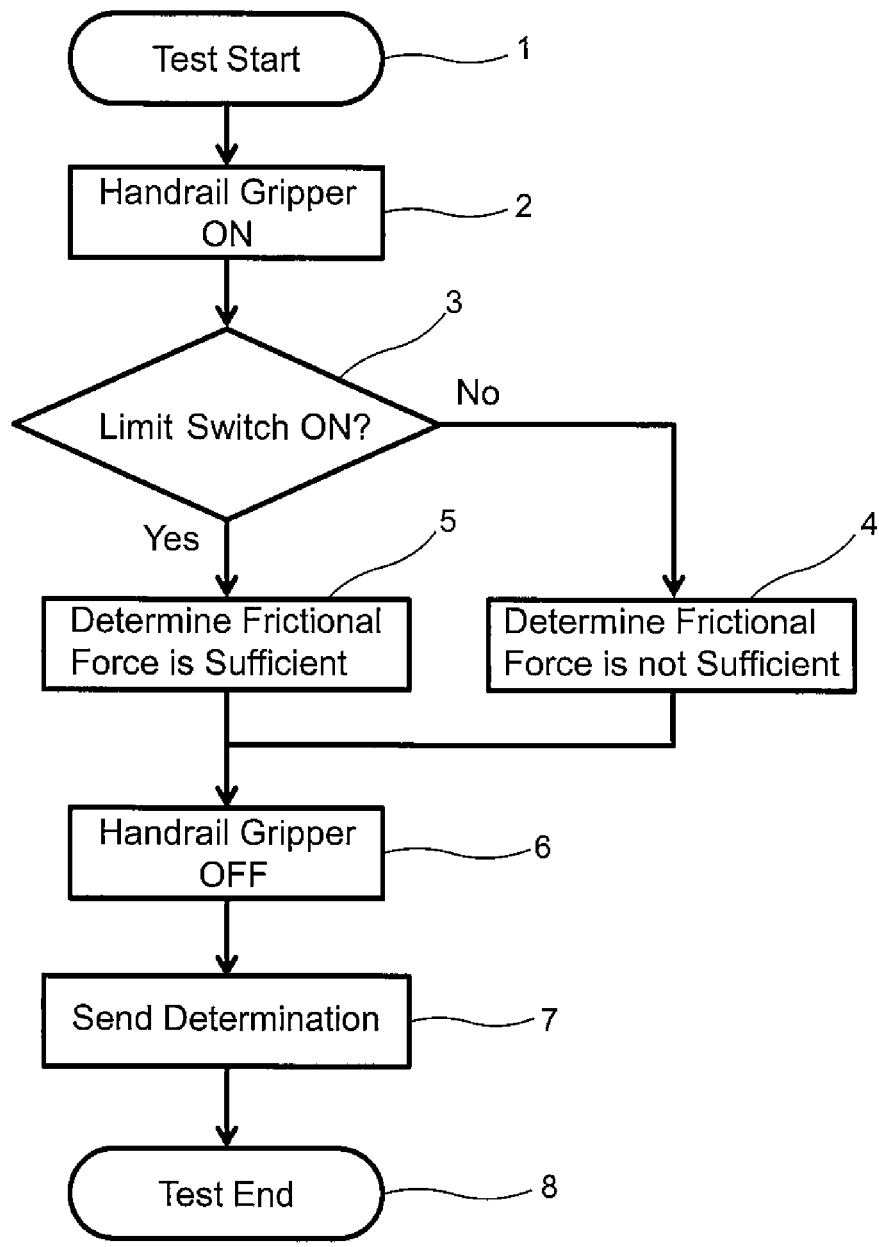
FIG. 7 is a flowchart showing a control sequence of a test conducted using the handrail friction checking device.

FIG. 7 is a flowchart showing a control sequence of a test conducted using the handrail friction checking device 12 of the present invention. The test is started at step 1 and the handrail gripper 20 is subsequently energized at step 2. In step 3, it is checked if the limit switch 15 is ON after a predetermined time delay. If "No", it is determined that the frictional driving force $F_2$ is not sufficient at step 4. If "Yes", it is determined that there is a sufficient frictional driving force $F_2$ at step 5. From steps 4 and 5 the sequence proceeds to step 6 at which the handrail gripper 20 is de-energized. Then, the determination made in step 4 or 5 is sent to a remote control center or a mobile device of a service engineer at step 7 and the test ends at step 8.

The test may be performed remotely from the remote control center during times of day the passenger conveyor 1 is not operating such as midnight. The test may also be performed at the site via a mobile device carried by a service engineer.

Figure 8:
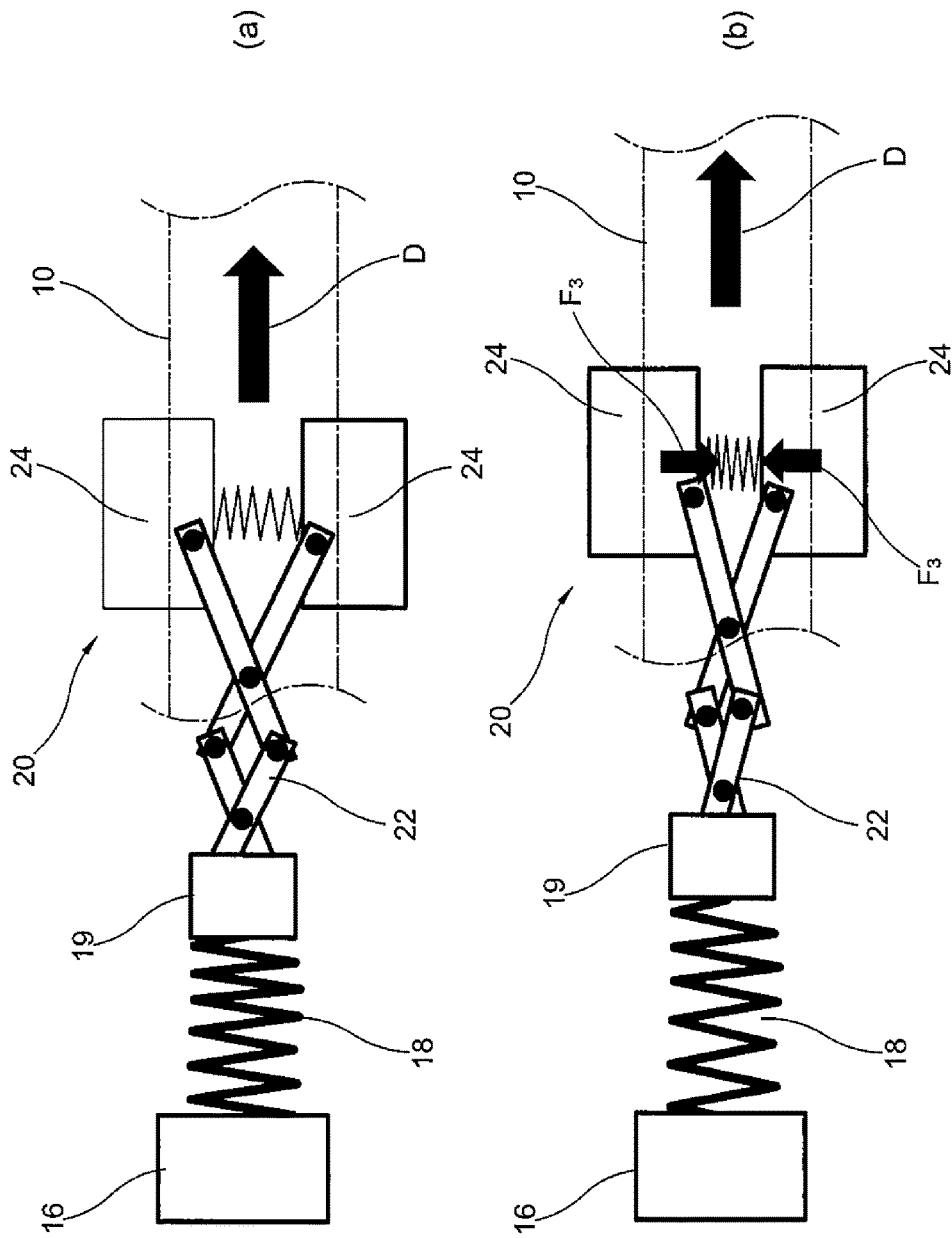
FIG. 8 is a plan view of the load applying device of FIG. 3 showing the movement of a connecting member.

FIG. 8 shows how the pantograph 22 contributes to further clamp the handrail 10 when the handrail gripper 20 grips the handrail 10. FIG. 8(a) shows the load applying device 14 with the handrail gripper 20 in a de-energized state. In FIG. 8(b), the handrail gripper 20 is energized to firmly grip the handrail 10. As the handrail gripper 20 travels with the handrail 10 in direction D, the pantograph 22 elongates such that a component force $F_3$ develops on the inner surface 24a of the gripping elements 24. The component force $F_3$ acts to further clamp the handrail 10 between the gripping elements 24.

Figure 9:
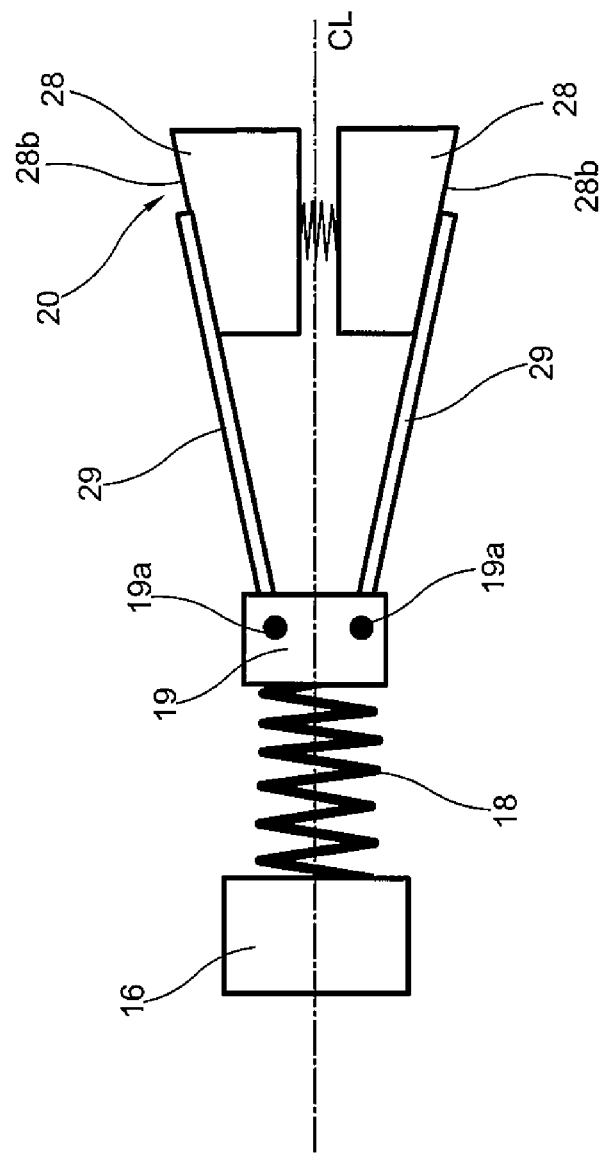
FIG. 9 is a plan view of another embodiment of a load applying device of the present invention.

FIG. 9 shows another embodiment of the load applying device 14 in which the gripping elements 28 each have an inclined outer surface 28b and the connecting member 22 is a pair of plates 29. Each of the plates 29 are attached to an inclined outer surface 28b of a respective gripping element 28 at one end and are pivotally connected to the intermediate member 19 via a pin 19a at the other end. The plates 29 are inclined with respect to a center line CL. Similar to the embodiment including the pantograph 22, a component force $F_3$ develops on the inner surface of the gripping elements 28 to further clamp the handrail 10 between the gripping elements 28.

Figure 10:
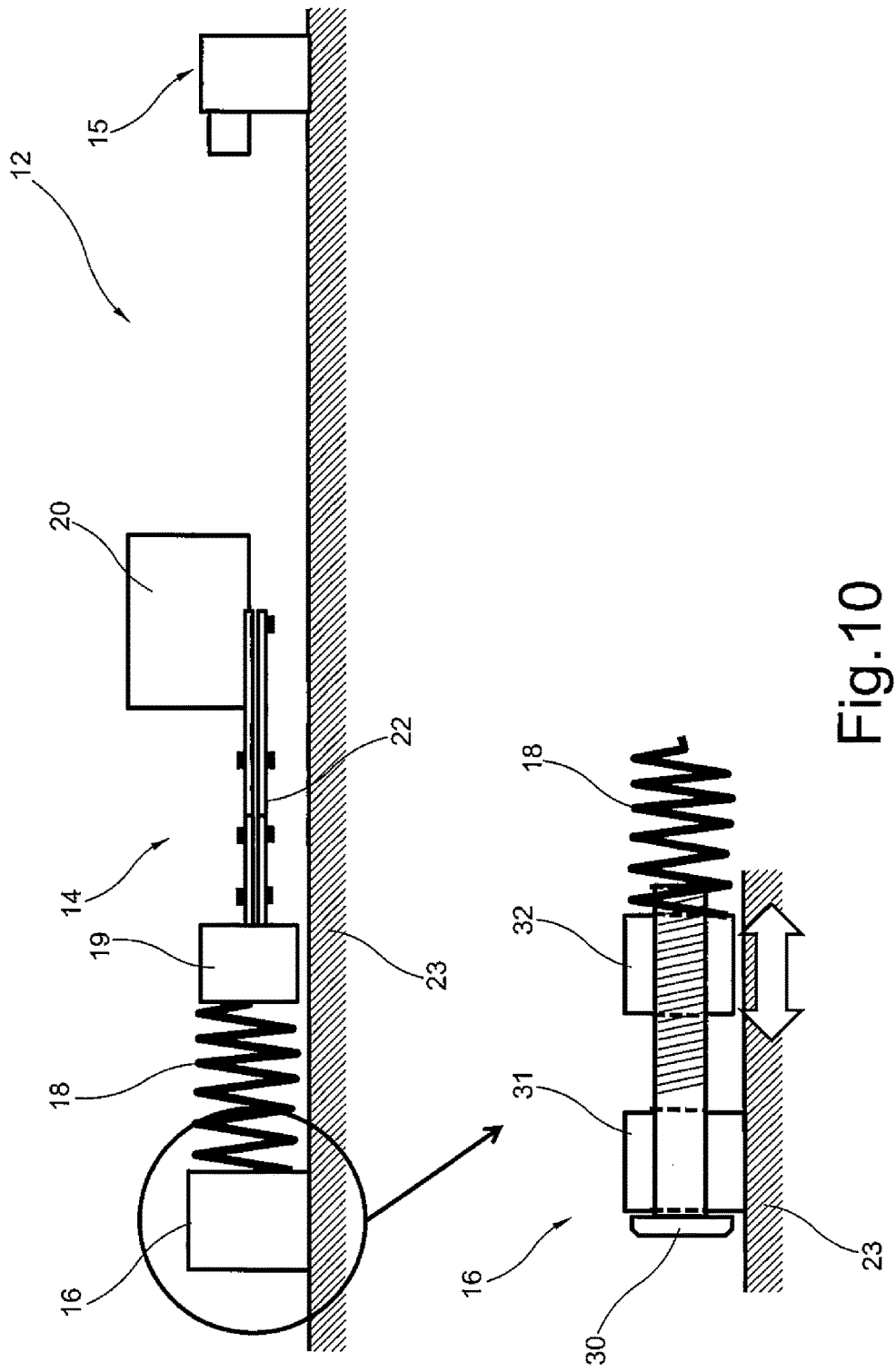
FIG. 10 is a side view of another embodiment of a handrail friction checking device of the present invention.

As shown in FIG. 10, the spring force $F_1$ may be adjustable. The base 16 may comprise a bolt 30 and a mounting member 31 attached to a structural component 23 of the truss 4. The bolt 30 is rotatable within the mounting member 31 and is screwed into a nut 32 to which the coil spring 18 is connected. By rotating the bolt 30, the distance between the coil spring 18 and the limit switch 15 may be changed to adjust the spring force $F_1$.

Figure 11:
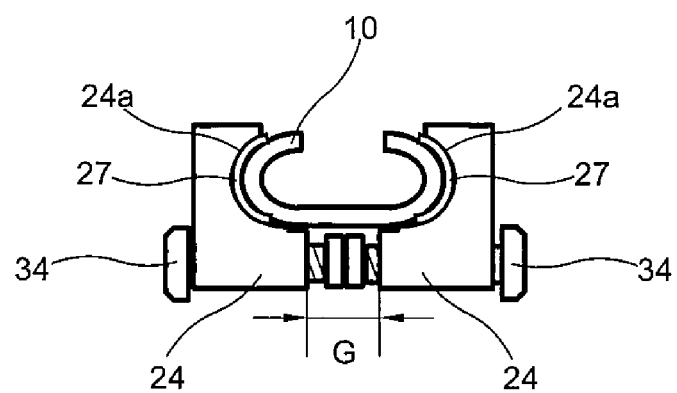
FIG. 11 is a schematic view of another embodiment of a handrail gripper of the present invention.

As shown in FIG. 11, the lateral gap G between the gripping elements 24 may also be adjusted. The gap G may be adjusted by bolts 34. Since the handrail 10 must slide along the handrail guide 11 during testing, the gripping force of the gripping elements 24 should not be too strong such that the gripping elements 24 clamp the handrail 10 against the handrail guide 11. By adjusting the gap G between the gripping elements 24, the gripping force of the handrail gripper 20 may be adjusted such that the handrail 10 is firmly gripped but slides along the handrail guide 11 during testing.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A handrail friction checking device, comprising:
   a handrail gripper for gripping a handrail and movable together with the handrail;
   a spring, one end of said spring being fixed and the other end being connected to the handrail gripper, said spring configured to apply a spring force which is opposed to the direction of handrail movement to the handrail gripper when the handrail gripper moves along with the handrail; and a sensor which is disposed at a distance from said handrail gripper, the sensor configured to be triggered by the handrail gripper when the handrail gripper moves along with the handrail;

wherein it is determined there is slippage between the handrail and a handrail drive mechanism when the sensor is not triggered.

2. The handrail friction checking device of claim 1, wherein the handrail gripper comprises a pair of gripping elements which grip the handrail in between and are biased by a second spring.

3. The handrail friction checking device of claim 2, wherein at least one of the gripping elements includes an electromagnet.

4. The handrail friction checking device of claim 3, wherein one of the gripping elements includes an electromagnet and the other of the gripping elements includes an iron portion.

5. The handrail friction checking device of claim 3, wherein the handrail freely moves through the gripping elements during normal operation and the gripping elements grip the handrail when the electromagnet is energized.

6. The handrail friction checking device of claim 1, wherein the spring is a coil spring.

7. The handrail friction checking device of claim 1, wherein the spring force is adjustable.

8. The handrail friction checking device of claim 1, wherein the sensor is a limit switch.

9. The handrail friction checking device of claim 1, further comprising:
   a base fixed to a structural component and connected to one end of the spring;
   an intermediate member connected to the other end of the spring; and
   a connecting member connecting the intermediate member to the handrail gripper.

10. The handrail friction checking device of claim 9, wherein the connecting member comprises a pantograph.

11. The handrail friction checking device of claim 9, wherein the handrail gripper comprises a pair of gripping elements and the connecting member comprises a pair of inclined plates with one end attached to a respective gripping element and the other end pivotally connected to the intermediate member.

12. The handrail friction checking device of claim 1, wherein the handrail friction checking device is installed in a passenger conveyor.

* * * * *